(12) United States Patent
Al-Abed et al.

(10) Patent No.: US 8,741,924 B2
(45) Date of Patent: Jun. 3, 2014

(54) COMPOUNDS AND METHODS FOR TREATMENT OF SYSTEMIC LUPUS ERYTHEMATOSUS

(75) Inventors: Yousef Al-Abed, Dix Hills, NY (US); Betty A. Diamond, Bronx, NY (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 0 days.

(21) Appl. No.: 13/696,326

(22) PCT Filed: May 6, 2011

(86) PCT No.: PCT/US2011/000799
§ 371 (c)(1),
(2), (4) Date: Dec. 21, 2012

(87) PCT Pub. No.: WO2011/139378
PCT Pub. Date: Nov. 10, 2011

(65) Prior Publication Data
US 2013/0123299 A1    May 16, 2013

Related U.S. Application Data

(60) Provisional application No. 61/343,969, filed on May 6, 2010.

(51) Int. Cl.
*A61K 31/47*    (2006.01)
*C07D 401/02*   (2006.01)

(52) U.S. Cl.
USPC ........... 514/307; 514/314; 546/139; 546/140; 546/150; 546/164

(58) Field of Classification Search
None
See application file for complete search history.

(56) References Cited

U.S. PATENT DOCUMENTS

| | | |
|---|---|---|
| 6,479,504 B1 | 11/2002 | Macfarlane et al. |
| 6,916,830 B2 | 7/2005 | Lee et al. |
| 2006/0088545 A1 | 4/2006 | Ensoli |
| 2010/0099673 A1 | 4/2010 | Bilodeau et al. |

OTHER PUBLICATIONS

PCT International Search Report dated Jul. 21, 2011 in connection with PCT International Patent Application No. PCT/US2011/00799, 4 pages.
PCT Written Opinion of the International Searching Authority dated Jul. 21, 2011 in connection with PCT International Patent Application No. PCT/US2011/00799, 4 pages.
Fortovase (saquinavir)—Complete product information—Roche pharmaceuticals Inc., Dec. 2003, 31 pages.

*Primary Examiner* — Zinna Northington Davis
(74) *Attorney, Agent, or Firm* — Amster, Rothstein & Ebenstein LLP

(57) ABSTRACT

Small molecule compounds are provided for treating lupus as are methods of treating lupus using these compounds.

26 Claims, 8 Drawing Sheets

Compound 12W

WEY

COMPOUNDS AND METHODS FOR TREATMENT OF SYSTEMIC LUPUS ERYTHEMATOSUS

CROSS-REFERENCE TO RELATED APPLICATIONS

This application is a U.S. national stage entry under 35 U.S.C. §371 of PCT International Patent Application No. PCT/US2011/000799, filed May 6, 2011, which claims priority to U.S. Provisional Patent Application No. 61/343,969, filed May 6, 2010, the contents of which are incorporated herein by reference in their entirety.

FIELD OF THE INVENTION

The present invention relates generally to compounds and methods for treating systemic lupus erythematosus (SLE).

BACKGROUND OF THE INVENTION

Throughout this application various publications are referred to in parenthesis. Full citations for these references may be found at the end of the specification. The disclosures of these publications are hereby incorporated by reference in their entirety into the subject application to more fully describe the art to which the subject invention pertains.

Systemic lupus erythematosus (SLE) is a chronic autoimmune disease affecting an estimated 5 million people worldwide, primarily young woman. SLE is characterized by the presence of pathogenic autoantibodies, many of which are directed against nuclear antigens, in particular double stranded (ds) DNA. Clinical studies as well as animal models have shown that anti-dsDNA antibodies contribute to kidney disease. A subset of anti-DNA antibodies cross-reacts with the N methyl D aspartate receptor (NMDAR) on neurons and in the kidney. These autoantibodies are both neurotoxic and nephrotoxic and are present in approximately 30-40% of lupus patient sera and in cerebrospinal fluid (CSF) of patients with central nervous system (CNS) manifestations of SLE. The present invention address the need for small molecule compounds that can be used for the treatment of lupus.

SUMMARY OF THE INVENTION

The present invention provides a compound having the structure:

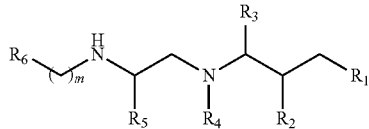

wherein: m=1-6; $R_1$ is quinoline or isoquinoline, partially or fully hydrated, and optionally substituted with R', OR', SR', $(CH_2)_n NHR'$ or $(CH_2)_n N(R')_2$, wherein n'=0-6, and R' is independently H, or branched or unbranched $C_{1-6}$ alkyl or heteroalkyl; $R_2$ is (i) keto or thioketo; or (ii) R", OR", SR", NHR" or $N(R")_2$, wherein R" is independently H, or branched or unbranched $C_{1-6}$ alkyl or heteroalkyl; $R_3$ and $R_4$ are, independently, H or $(CH_2)_n R$ where R is aryl and n=1-6; $R_5$ is $(CH_2)_{n'''} N(R_3)_2$ or $(CH_2)_{n'''} COX$ wherein X is R''', OR''', SR''', NHR''' or $N(R''')_2$, wherein n'''=0-6, and R''' is independently H, or branched or unbranched $C_{1-6}$ alkyl or heteroalkyl; and $R_6$ is quinoline or isoquinoline, partially or fully hydrated, and optionally substituted with $R^{IV}$, $OR^{IV}$, $SR^{IV}$, $(CH_2)_{n_{IV}}NHR^{IV}$ or $(CH_2)_{n_{IV}}N(R^{IV})_2$, wherein $n^{IV}$=0-6, and $R^{IV}$ is independently H, or branched or unbranched $C_{1-6}$ alkyl or heteroalkyl; or a pharmaceutically acceptable salt thereof.

The invention further provides methods of treating systemic lupus erythematosus (SLE) in a subject in need thereof comprising administering any of the compounds disclosed herein to the subject in an amount and manner effective to treat SLE.

DETAILED DESCRIPTION OF THE INVENTION

Figure 1A:
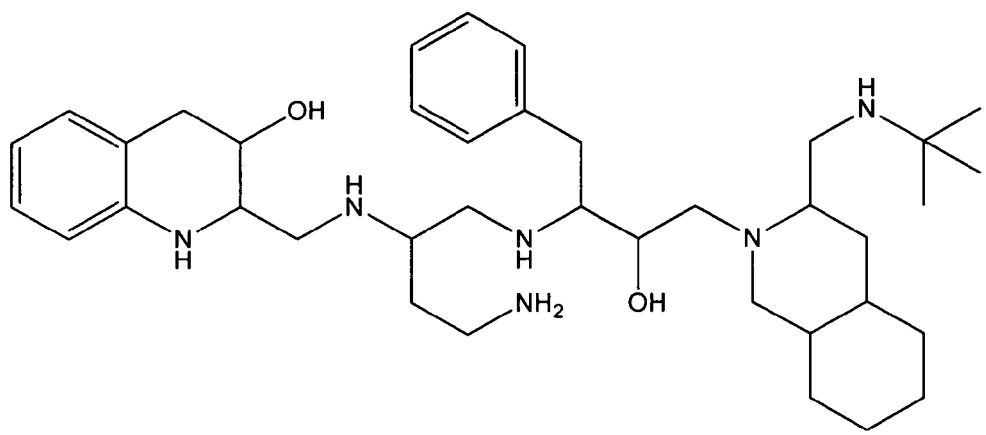
FIG. 1A-1E. Compound 12W inhibits antigen recognition by systemic lupus erythematosus (SLE) autoantibodies. A) Structures of Compound 12W and WEY peptide (i.e., a tripeptide identical to the pentapeptide DWEYS (SEQ ID NO:1) less the carboxyl serine residue and the amino terminal aspartate of the pentapeptide). B) R4A mouse autoantibody binding to DWEYS (SEQ ID NO:1) peptide. C) R4A mouse autoantibody binding to DNA. D) G11 human autoantibody binding to DWEYS (SEQ ID NO:1) peptide. E) G11 human autoantibody binding to DNA. In B)-E), antibody binding in the presence of DWEYS peptide is shown in the right plot in each figure. Compound 12W inhibits binding as shown by the left plot in each figure.
Figure 1A:
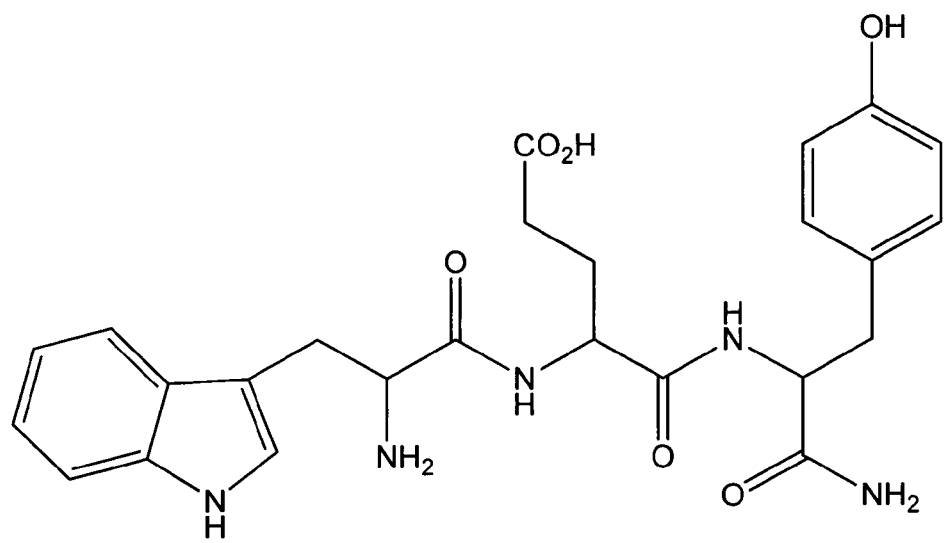

The present invention provides a compound having the structure:

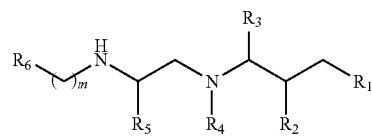

wherein:
m=1-6;
$R_1$ is quinoline or isoquinoline, partially or fully hydrated, and optionally substituted with R', OR', SR', $(CH_2)_n NHR'$ or $(CH_2)_n N(R')_2$, wherein n'=0-6, and R' is independently H, or branched or unbranched $C_{1-6}$ alkyl or heteroalkyl;

$R_2$ is (i) keto or thioketo; or (ii) R", OR", SR", NHR" or $N(R")_2$, wherein R" is independently H, or branched or unbranched $C_{1-6}$ alkyl or heteroalkyl;

$R_3$ and $R_4$ are, independently, H or $(CH_2)_n R$ where R is aryl and n=1-6;

$R_5$ is $(CH_2)_{n'''} N(R_3)_2$ or $(CH_2)_{n'''} COX$ wherein X is R''', OR''', NHR''' or $N(R''')_2$, wherein n'''=0-6, and R''' is independently H, or branched or unbranched $C_{1-6}$ alkyl or heteroalkyl; and $R_6$ is quinoline or isoquinoline, partially or fully hydrated, and optionally substituted with $R^{IV}$, $OR^{IV}$, $SR^{IV}$, $(CH_2)_{nIV}NHR^{IV}$ or $(CH_2)_{nIV}N(R^{IV})_2$, wherein $n^{IV}$=0-6, and $R^{IV}$ is independently H, or branched or unbranched $C_{1-6}$ alkyl or heteroalkyl;

or a pharmaceutically acceptable salt thereof.

In any of the compounds disclosed herein, $R_1$ is preferably isoquinoline, partially or fully hydrated, and optionally substituted with R', OR', SR', $(CH_2)_nNHR'$ or $(CH_2)_nN(R')_2$, wherein n'=0-6, and R' is independently H, or branched or unbranched $C_{1-6}$ alkyl or heteroalkyl. Preferably, in $R_1$, isoquinoline is fully hydrated. Preferably, in $R_1$, isoquinoline is substituted with $(CH_2)_nNHR^1$ or $CH_2NHR'$. Preferably, R' is branched or unbranched $C_{1-6}$ alkyl, and more preferably, R' is branched $C_4$ alkyl. Preferred compounds include those in which $R_1$ has the structure

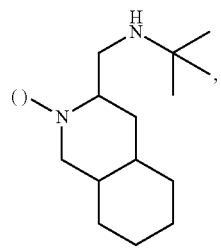

where ( ) represents the point of attachment to the molecular scaffold.

In any of the compounds disclosed herein, $R_2$ is preferably R'' or OR'', and more preferably, $R_2$ is OH.

In any of the compounds disclosed herein, $R_3$ is preferably $(CH_2)_nR$, and more preferably $R_3$ is benzyl.

In any of the compounds disclosed herein, $R_4$ is preferably H.

In any of the compounds disclosed herein, $R_5$ is preferably $(CH_2)_{n'''}N(R_3)_2$, and more preferably $R_5$ is $(CH_2)_2NH_2$.

In any of the compounds disclosed herein, m is preferably 1.

In any of the compounds disclosed herein, $R_6$ is preferably quinoline, partially or fully hydrated, and optionally substituted with $R^{IV}$, $OR^{IV}$, $SR^{IV}$, $(CH_2)_{nIV}NHR^{IV}$ or $(CH_2)_{nIV}N(R^{IV})_2$, wherein $n^{IV}$=0-6, and $R^{IV}$ is independently H, or branched or unbranched $C_{1-6}$ alkyl or heteroalkyl. Preferably, in $R_6$, quinoline is partially hydrated. Preferably, in $R_6$, the partially hydrated quinoline is 1,2,3,4-tetrahydroquinoline. Preferably, in $R_6$, quinoline is substituted with $R^{IV}$ or $OR^{IV}$, and more preferably in $R_6$, quinoline is substituted with OH. Preferred compounds include those in which $R_6$ has the structure

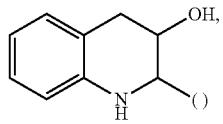

where ( ) represents the point of attachment to the molecular scaffold.

Preferred compounds include a compound (referred to herein as Compound 12W or 12W) having the structure:

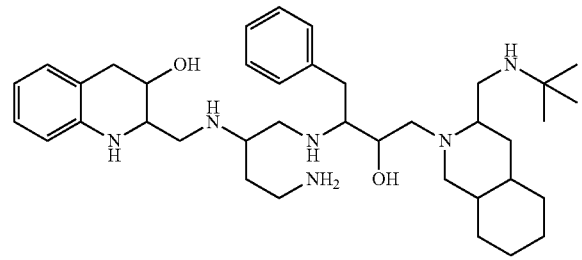 [SMILES: CC(C)(C)NCC1CC2CCCCC2CN1CC(O)C(Cc1ccccc1)NCC(CCN)NCC1Nc2ccccc2CC1O]

(2-((4-amino-1-(4-(3-((tert-butylamino)methyl)octahydroisoquinolin-2(1H)-yl)-3-hydroxy-1-phenylbutan-2-ylamino)butan-2-ylamino)methyl)-1,2,3,4-tetrahydroquinolin-3-ol), or a pharmaceutically acceptable salt thereof.

The compounds of the invention include specific optical isomers and stereoisomers of the structures disclosed herein. For instance, there are eight asymmetric carbon atoms in the preferred Compound 12W.

Pharmaceutically acceptable salts include non-toxic salts derived from inorganic or organic acids, including, for example, the following acid salts: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, p-toluenesulfonate, salicylate, succinate, sulfate, tartrate, thiocyanate, and undecanoate.

In different embodiments, the compounds disclosed herein can be tagged with a radioisotope or a toxin, or coupled to an antibody or Fc backbone.

The present invention also provides a pharmaceutical composition comprising any of the compounds disclosed herein and a pharmaceutically acceptable carrier. Pharmaceutically acceptable carriers include, but are not limited to, additive solution-3 (AS-3), saline, phosphate buffered saline, Ringer's solution, lactated Ringer's solution, Locke-Ringer's solution, Krebs Ringer's solution, Hartmann's balanced saline solution, and/or heparinized sodium citrate acid dextrose solution. The pharmaceutically acceptable carrier used can depend on the route of administration.

The invention further provides a method of treating systemic lupus erythematosus (SLE) in a subject in need thereof comprising administering any of the compounds disclosed herein to the subject in an amount and manner effective to treat SLE.

As used herein, to treat SLE in a subject means to stabilize, reduce or eliminate a sign or symptom of SLE in the subject. SLE most often harms the heart, joints, skin, lungs, blood vessels, liver, kidneys, and nervous system. Subjects with SLE can experience fever, malaise, joint pains, myalgias, fatigue, and temporary loss of cognitive abilities. SLE patients can suffer, for example, dermatological symptoms, such as the classic malar rash (or butterfly rash); hematological manifestations, such as anemia and iron deficiency and low platelet and white blood cell counts; inflammation of various parts of the heart, such as pericarditis, myocarditis, and endocarditis; lung and pleura inflammation; hematuria or proteinuria; and neuropsychiatric manifestation such as headache, cognitive dysfunction, mood disorder, cerebrovascular disease, seizures, polyneuropathy, anxiety disorder, and psychosis.

The compounds of the present invention can be formulated in a pharmaceutically acceptable carrier in unit dosage form. In this regard, pharmaceutical compositions useful for these embodiments can be formulated without undue experimentation for administration to a subject as appropriate for the desired mode of administration. Additionally, proper dosages of the compositions can be determined without undue experimentation using standard dose-response protocols.

Any acceptable route of administration can be used. Pharmaceutical compositions designed, for example, for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients. Tablets, pills, capsules, troches and the like may also contain binders, recipients, disintegrating agent, lubricants, sweetening agents, and flavoring agents.

Pharmaceutical compositions useful for the present invention can also be administered parenterally such as, for example, by intravenous, intramuscular, intrathecal or subcutaneous injection. Parenteral administration can be accomplished by incorporating the compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves and the like.

Nasal administration includes administering the composition to the mucous membranes of the nasal passage or nasal cavity of the patient. Pharmaceutical compositions for nasal administration include compositions prepared by well-known methods to be administered, for example, as a nasal spray, nasal drop, suspension, gel, ointment, cream or powder. Administration of the composition may also take place using a nasal tampon or nasal sponge.

The methods disclosed herein can be used with any mammal. Preferably, the mammal is a human.

The invention also provides for any of the compounds disclosed herein for use for treatment of systemic lupus erythematosus (SLE), and for the use of these compound for the preparation of a pharmaceutical composition for treatment of systemic lupus erythematosus (SLE).

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

The D form of the DWEYS (SEQ ID NO:1) peptide blocks renal deposition of DNA/NMDAR cross-reactive antibodies and prevents the excitotoxic neuronal death caused by these antibodies. In the present invention, structural features of the DWEYS (SEQ ID NO:1) peptide were used to design novel, selective and potent small molecules that bind anti-dsDNA/NMDAR lupus autoantibodies in vitro, preventing their interaction with tissue antigen. Compound 12W blocked autoantibody binding to renal tissue both ex vivo and in vivo and protected against lupus autoantibody-induced neurotoxicity in vivo. Such small molecule compounds have therapeutic potential for the treatment of lupus.

While multiple species of autoantibodies can contribute to SLE pathogensis, antibodies to dsDNA are essentially diagnostic of the disease, correlate with disease activity and have been eluted from kidneys of patients with nephritis. Once bound to tissue, anti-dsDNA antibodies trigger tissue damage by a variety of mechanisms including activation of complement components with an ensuing inflammatory cascade and engagement of Fc receptors (FcR) with activation of FcR-bearing cells. Studies of nephritogenic antibodies have shown that many bind glomeruli even after the tissue has been treated with DNase. Anti-dsDNA antibodies have been shown to have substantial cross-reactivity with biomolecules other than dsDNA (e.g., proteins), which contributes to their pathogenicity. Moreover, anti-DNA antibodies form immune complexes containing DNA, which will activate dendritic cells and other cell types through the toll-like receptor 9 pathway.

Previously, a search for cross-reactive antigens seen by a mouse monoclonal anti-dsDNA antibody, R4A, identified a consensus sequence DWEYSG (SEQ ID NO:2) (Gaynor et al. 1997). The consensus sequence is present in both the NR2A and NR2B subunits of the mouse and human NMDAR (DiGiorgio et al. 2001). R4A binds glomeruli and NMDARs and causes neuronal death through apoptosis when microinjected intracerebrally in mice (DeGiorgio et al. 2001). Mice immunized with a multimerized version of DWEYS (SEQ ID NO:1) antigen to elicit anti-DNA/NMDAR antibodies display glomerular Ig deposition but no neuronal damage until a breach of the blood brain barrier allows transit of these antibodies into the CNS (Kowal et al. 2004). Anti-dsDNA antibodies that recognize the DWEYS (SEQ ID NO:1) peptide have been demonstrated to be present in 40-50% of lupus sera and in the CSF in a high percentage of lupus patients with neuropsychiatric lupus. When mice are given anti-DNA/NMDAR antibodies isolated from human SLE sera intravascularly followed by lipopolysaccharide to induce a breach of the blood-brain barrier, they exhibit neuronal death accompanied by cognitive impairment demonstrating that antibodies with this specificity in the circulation of lupus patients are potentially neurotoxic (Kowal et al. 2006, Huerta et al. 2006). Studies have also shown that gestating mice harboring anti-DNA/NMDAR antibodies in their circulation give birth to offspring with impaired brain development (Lee et al. 2009).

In vivo administration of the DWEYS (SEQ ID NO:1) peptide blocks renal and brain deposition of anti-DNA/NMDAR antibodies in mice (Gaynor et al. 1997, Huerta et al. 2006). Taken together, these studies identified both the pathogenicity of the anti-DNA/NMDAR antibodies present in lupus patients and the possible clinical utility of the DWEYS (SEQ ID NO:1) peptide.

Structural features of the DWEYS (SEQ ID NO:1) peptide were used to design a novel small molecule (Compound 12W) that would act as a peptide mimetope and function as an antagonist of anti-dsDNA/NMDAR lupus antibodies (FIG. 1A).

Chemical Synthesis

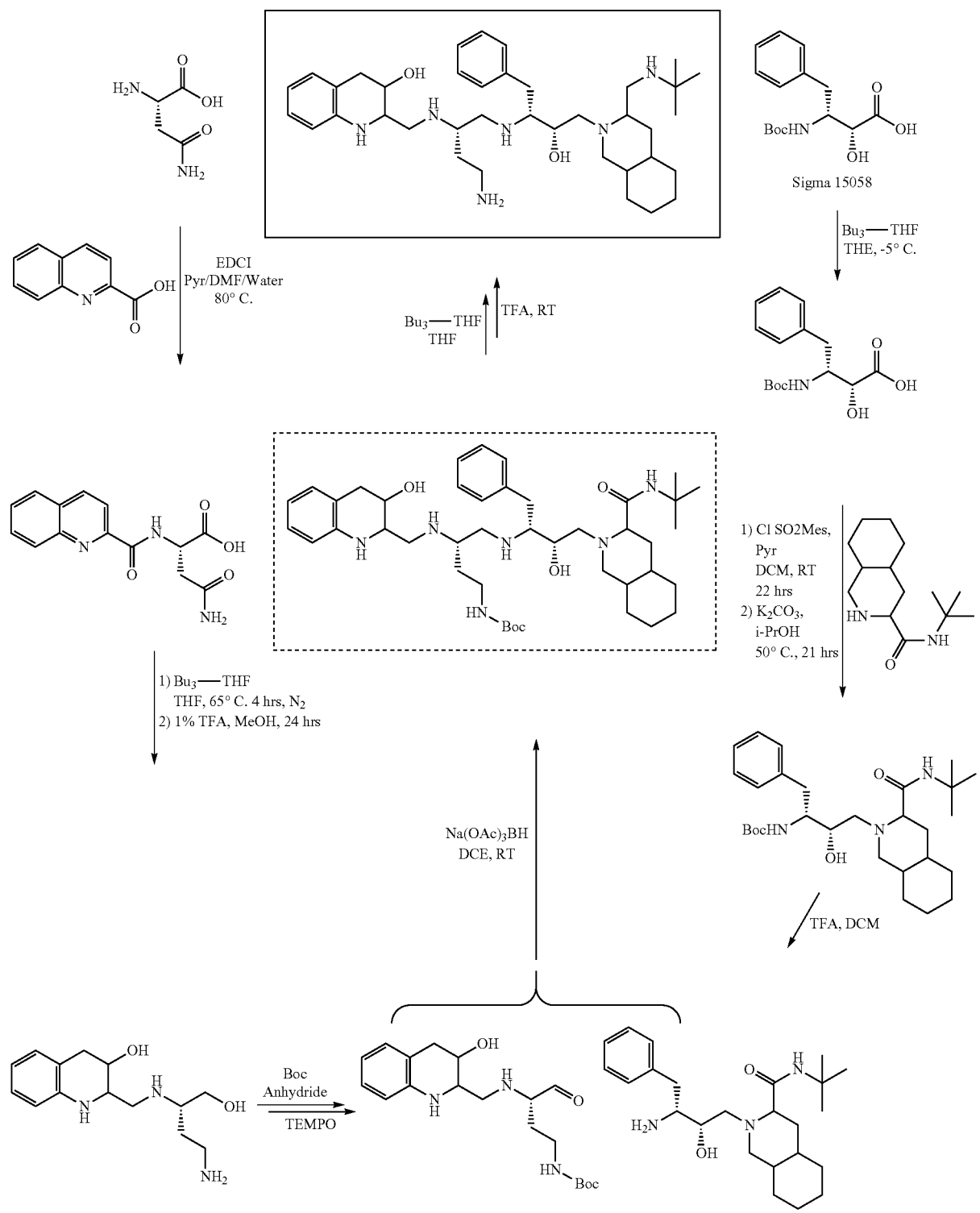

Results

Figure 1B:
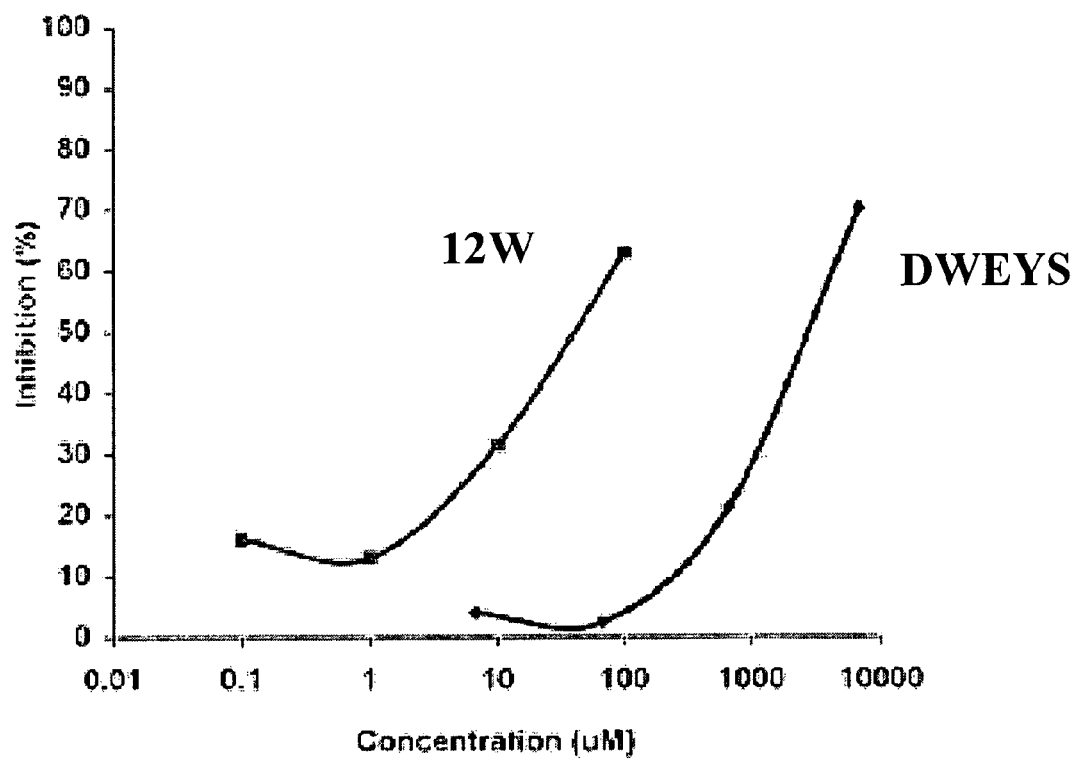
Figure 1C:
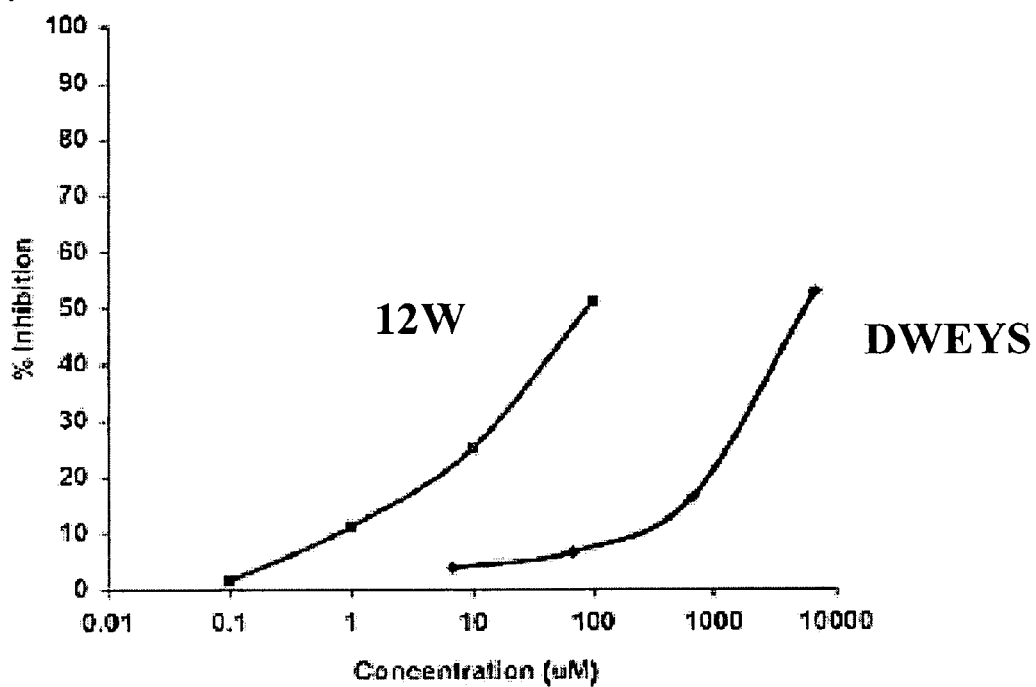
Figure 1D:
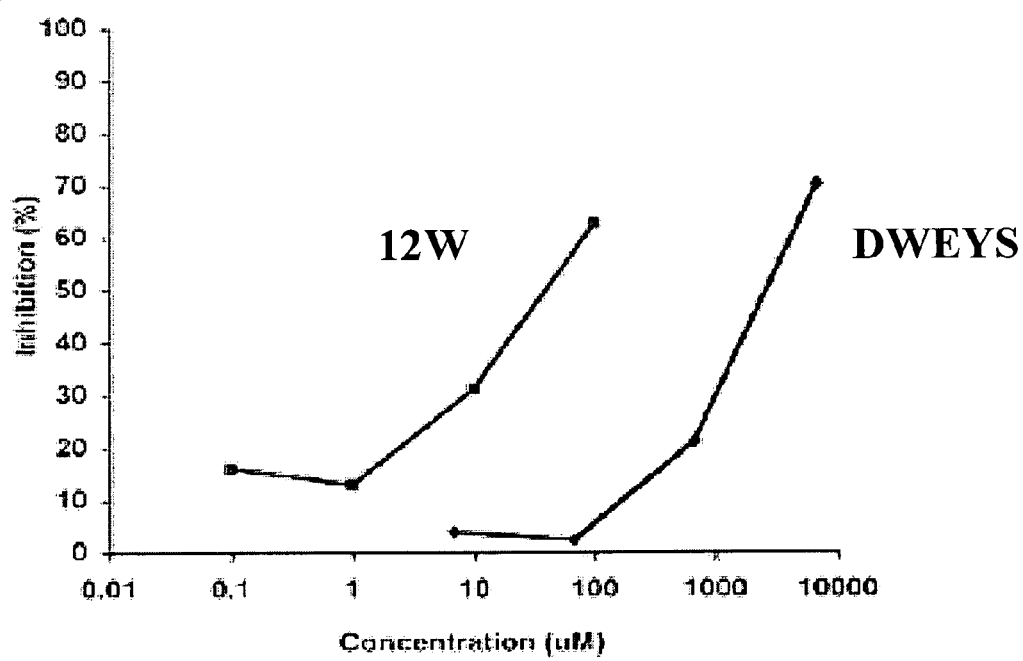
Figure 1E:
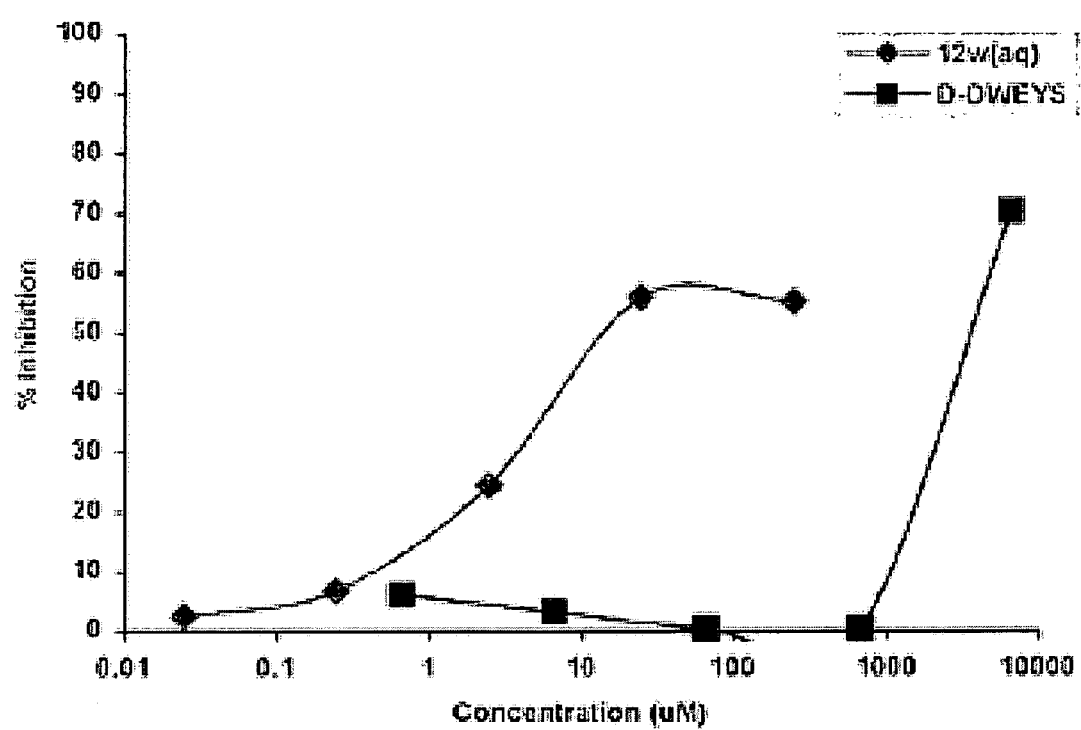

As shown previously, in vitro R4A binding to its known antigens, the DWEYS (SEQ ID NO:1) peptide or dsDNA was inhibitable by DWEYS (SEQ ID NO:1) peptide at mM concentrations (FIGS. 1B and C, right plot in each figure). In comparison, Compound 12W was able to inhibit R4A binding to these same antigens at nM concentrations (FIGS. 1B and C, left plot in each figure). This inhibition was specific for the interaction between R4A and its antigens, as Compound 12W failed to inhibit binding of an anti-BSA antibody to BSA (data not shown). A previous study showed that the G11 antibody cloned from a peripheral blood B cell of a lupus patient bound dsDNA, DWEYS (SEQ ID NO:1) peptide, and NMDAR. Therefore, it was tested whether Compound 12W could similarly inhibit binding of G11 to its known antigens in a competitive ELISA. Indeed, Compound 12W inhibited G11 binding at similar concentrations to its effect on R4A binding (FIG. 1D, E).

Figure 2A:
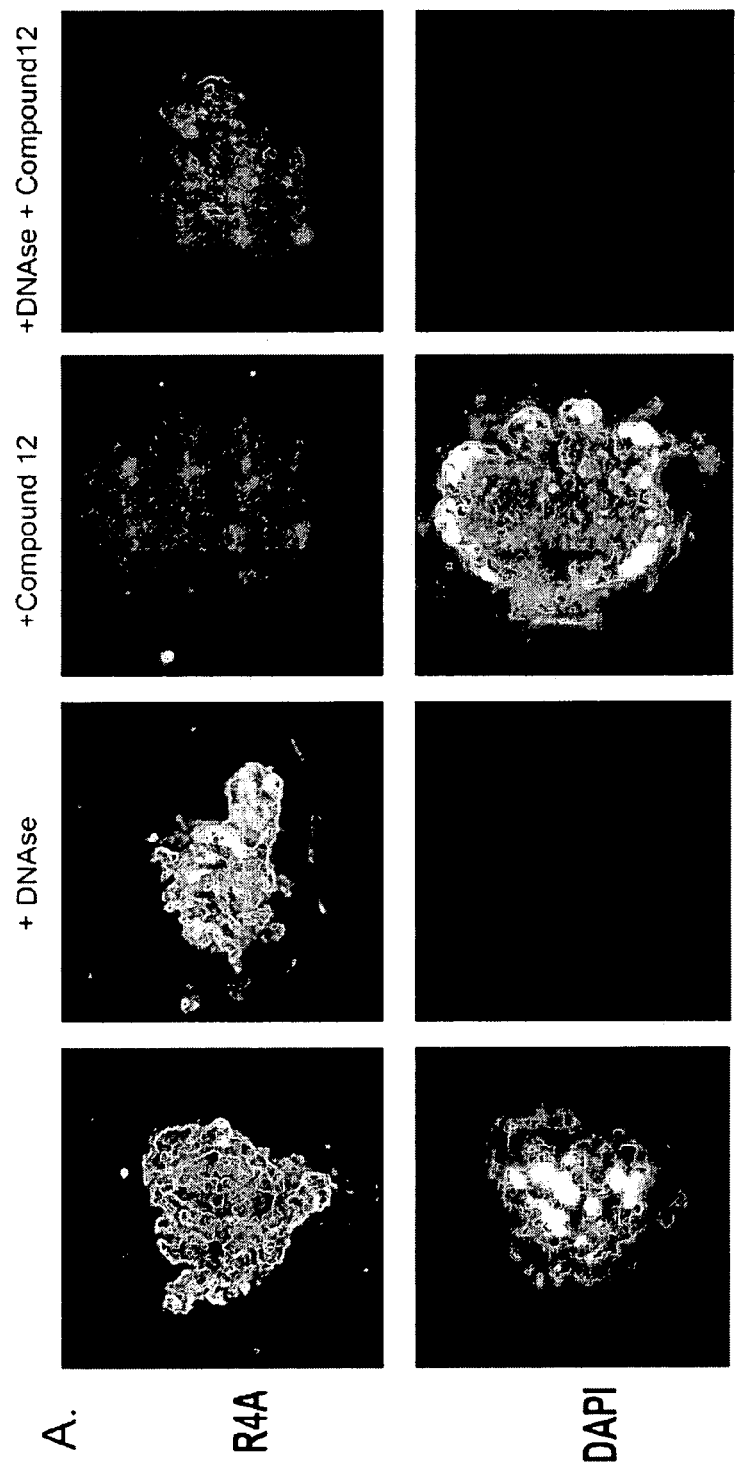
FIG. 2A-2B. Compound 12W inhibits SLE autoantibody binding to glomeruli in situ. A) Data with R4A. B) Data with G11. From left to right: control, +DNAse, +Compound 12W, +DNAse+Compound 12W.
Figure 2B:
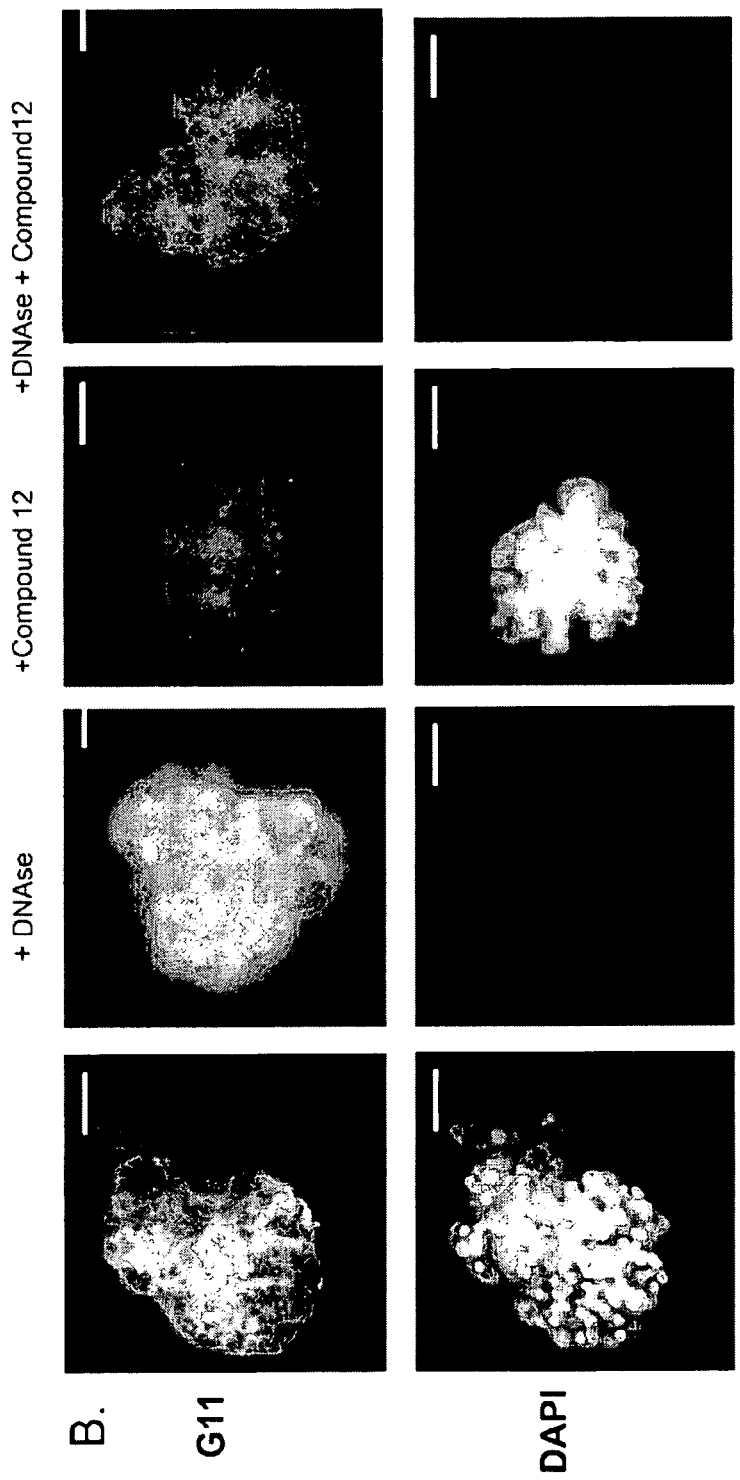

The kidney is a major target organ in SLE, with renal disease occurring in approximately 50% of patients. Glomerular deposition of circulating autoantibodies leads to a cascade of inflammatory events including renal infiltration by activated immune cells, activation of dendritic cells through Toll-like receptors and pro-inflammatory cytokine production (Bagavant and Fu 2009), which can culminate in end-stage renal disease. Pathogenic human and mouse lupus autoantibodies have been shown to bind to kidney glomeruli ex vivo. The R4A and G11 antibodies, as well as other pathogenic lupus antibodies, bind to both DNA and non-DNA antigens present in kidney glomeruli ex vivo. Glomerular binding by R4A can be blocked by the DWEYS (SEQ ID NO:1) peptide (Gaynor et al 1997). To test if Compound 12W could block the binding of the R4A antibody to its renal antigens in situ, the R4A antibody was incubated with mouse kidney glomeruli in the presence and absence of Compound 12W and its binding measured by detection with fluorescently-conjugated secondary antibodies. As demonstrated previously, R4A bound to glomeruli in the presence and absence of DNAse, reflecting its ability to recognize both DNA and non-DNA antigens (FIG. 2A, left panels). Dramatically less binding was observed to both DNA and non-DNA antigens when the R4A antibody was pre-incubated with Compound 12W (FIG. 2A, right panels). This inhibition was dependent on the dose of Compound 12W and could be mimicked by pre-incubation of the R4A antibody with the DWEYS (SEQ ID NO:1) peptide at mM concentrations (data not shown). A similar inhibition of binding to renal tissue was observed when the human autoantibody G11 was incubated in the presence of Compound 12W, (FIG. 2B), further supporting the therapeutic potential of the compound.

Figure 3:
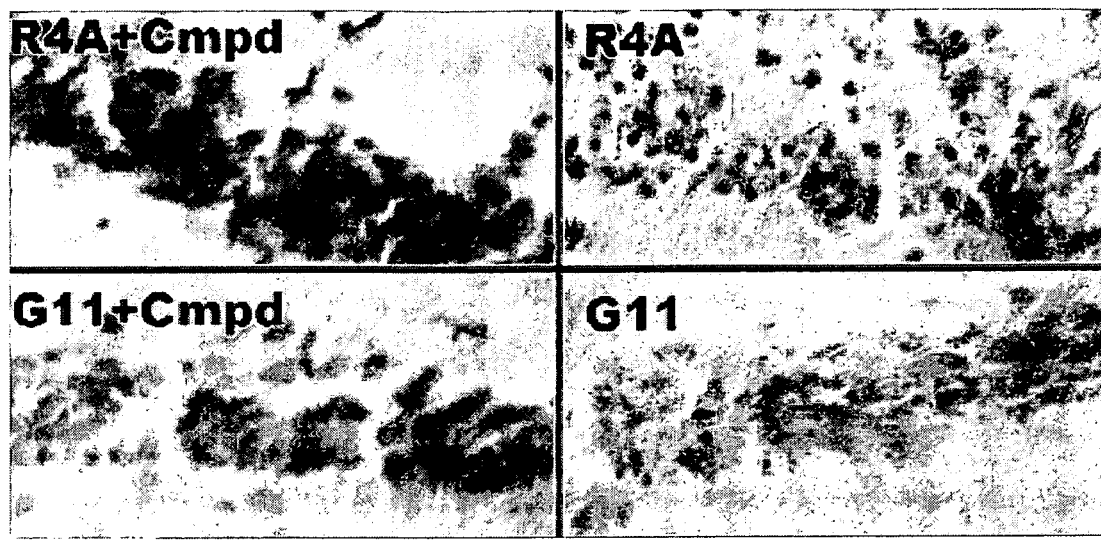
FIG. 3. Compound 12W inhibits neurotoxicity of autoantibodies. The lupus autoantibodies caused significant neuronal apoptosis, as indicated by positive TUNEL staining (right panels). In contrast, co-administration with Compound 12W blocked the neurotoxic effects of the lupus antibodies (left panels).

Both R4A and G11 cause excitotoxic death of neurons in the mouse hippocampus (Zhang et al. 2009). Therefore, the ability of Compound 12W to negate the neurotoxicity of these autoantibodies was assayed. To test the neuroprotective potential of Compound 12W, mice were injected intracerebrally with R4A or G11 antibodies in the presence and absence of Compound 12W. As shown previously, the lupus autoantibodies caused significant neuronal apoptosis, as indicated by positive TUNEL staining (FIG. 3, upper and lower right panels). In contrast, co-administration with Compound 12W blocked the neurotoxic effects of the lupus antibodies (FIG. 3, upper and lower left panels). The neuroprotective dose of Compound 12W was 2 logs less than that previously used to achieve similar neuroprotection with the DWEYS (SEQ ID NO:1) peptide (Huerta et al. 2006).

Figure 4:
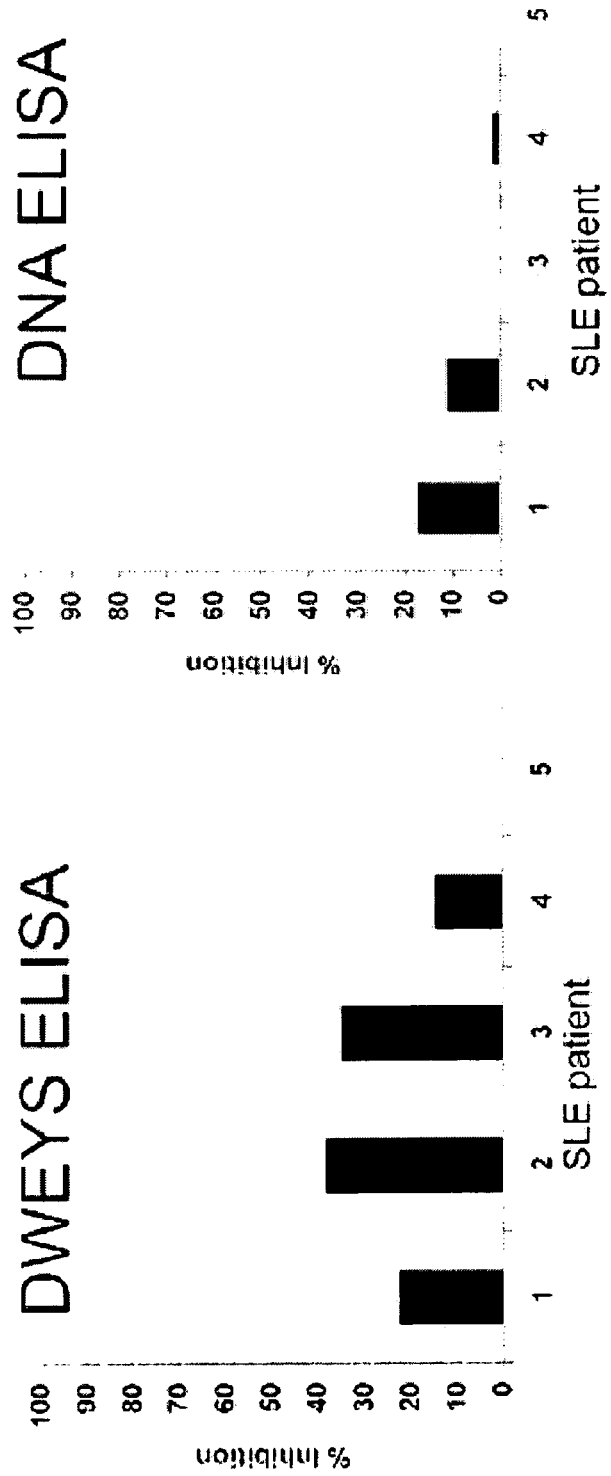
FIG. 4. Compound 12W inhibits autoantibodies present in human SLE sera. Inhibition of human SLE sera binding to antigens in vitro.

The studies above tested the ability of Compound 12W to neutralize monoclonal antibodies derived from mouse or human lupus sera. It was next tested whether Compound 12W would be similarly effective in inhibiting the polyclonal autoreactivity present in lupus patient sera (FIG. 4). Sera from lupus patients were pre-incubated with the Compound 12W and binding to DWEYS (SEQ ID NO:1) and dsDNA was then assayed in a competitive ELISA. As shown in FIG. 4, Compound 12W was able to inhibit binding to DWEYS (SEQ ID NO:1) peptide by autoantibodies present in serum from multiple lupus patients. The ability of Compound 12W to inhibit binding of lupus sera to mouse kidney glomeruli was also assayed. Similar to its inhibition of glomerular binding by monoclonal antibodies, Compound 12W blocked binding of human lupus sera to kidney antigens (data not shown).

Previously, co-administration of the DWEYS (SEQ ID NO:1) peptide was able to block binding of the anti-dsDNA antibodies to kidneys in vivo (Gaynor et al 1997). In order to test if Compound 12W was also effective at protecting the kidney, a major target organ in lupus, from antibody deposition, the anti-dsDNA/NMDAR G11/R4A/human lupus antibody was administered to SCID mice in the absence and presence of Compound 12W and glomerular deposition was measured.

Discussion

A small molecule has been identified that inhibits binding of lupus autoantibodies to both DNA and non-DNA antigens in vitro and in vivo. This compound is able to block a pathogenic antibody from target antigens in two major affected organs in lupus, the kidney and the brain.

Previously, four independent studies have used reagents coupled to the DWEYS (SEQ ID NO:1) peptide to target autoreactive B cells in lupus. The peptide was coupled to an antibody to FcRIIb, the inhibitory Fc receptor expressed on many cell types and the only Fc receptor expressed on B cells. This study provided evidence that such a reagent could be both preventative when give to lupus-prone mice and therapeutic, although the immunogenicity of the reagent eventually limited its utility. The DWEYS (SEQ ID NO:1) peptide was also coupled to an anti-CD35 (complement receptor 1) antibody; this reagent caused a selective decrease ex vivo in anti-DNA antibody secreting B cells from peripheral blood of lupus patients. More recently, both the DWEYS (SEQ ID NO:1) peptide and an epitope binding to CD22 were coupled to IgG. This reagent decreased titers of anti-DNA antibodies and improved renal survival in MRL/1 pr mice. An additional study described the effects of incorporating the DWEYS (SEQ ID NO:1) peptide and diphtheria toxin A into a pseudovirus; this reagent reduced anti-DNA antibodies and improved survival in another lupus-prone strain, NZB/W mice. In each case, the DWEYS (SEQ ID NO:1) peptide was used to target the appropriate B cell population. These studies are encouraging, but employ complicated biological reagents that would be difficult to manufacture and store, and could not be delivered orally. Also in each in vivo study the reagent while therapeutic, was also immunogenic. The present invention contemplates substitution of any of the compounds disclosed herein for the DWEYS (SEQ ID NO:1) peptide in any of the above reagents and applications.

The present identification of a novel small molecule that neutralizes antigen binding and the tissue-destructive activity of DWEYS (SEQ ID NO:1)-reactive autoantibodies circumvent these potential limitations. By translating some of the molecular features of the DWEYS (SEQ ID NO:1) peptide into a small molecule, one retains the antigenic specificity and gains in stability and potential for oral absorption and presumably escapes the production of neutralizing antibodies. Given that lupus therapies remain inadequate, the present invention provides for the development of more specific, less toxic therapies for lupus and a model for the development of therapeutics for other antibody-mediated symptoms or diseases.

REFERENCES

Bagavant H, Fu S M. Pathogenesis of kidney disease in systemic lupus erythematosus. Curr Opin Rheumatol. 21(5): 489-94, 2009.
DeGiorgio, L A et al. A subset of lupus anti-DNA antibodies cross-reacts with the NR2 glutamate receptor in systemic lupus erythematosus. Nat. Med. 7(11):1189-93, 2001.
Gaynor, B et al. Peptide inhibition of glomerular deposition of an anti-DNA antibody. Proc Natl Acad Sci USA 94:1955-60, 1997.
Huerta P T, et al. Immunity and behavior: antibodies alter emotion. Proc Natl Acad Sci USA. 103(3):678-83. Epub 2006 Jan. 4.
Kowal C, et al. Cognition and immunity; antibody impairs memory. Immunity 21(2): 179-88, 2004.
Kowal C, et al. Human lupus autoantibodies against NMDA receptors mediate cognitive impairment. Proc Natl Acad Sci USA. 103(52):19854-9. Epub 2006 Dec. 14.
Lee J Y, et al. Neurotoxic autoantibodies mediate congenital cortical impairment of offspring in maternal lupus. Nat. Med. 15(1):91-6, 2009. Epub 2008 Dec. 14.
Zhang J, et al. Polyreactive autoantibodies in systemic lupus erythematosus have pathogenic potential. J. Autoimmun. 33(3-4):270-4. Epub 2009 Apr. 26.

What is claimed is:

1. A compound having the structure:

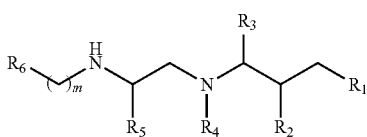

wherein:
m=1-6;
$R_1$ is quinoline or isoquinoline, partially or fully hydrated, and optionally substituted with R', OR', SR', $(CH_2)_{n'}NHR'$ or $(CH_2)_{n'}N(R')_2$, wherein n'=0-6, and R' is independently H, or branched or unbranched $C_{1-6}$ alkyl or heteroalkyl;
$R_2$ is (i) keto or thioketo; or (ii) R", OR", SR", NHR" or $N(R")_2$, wherein R" is independently H, or branched or unbranched $C_{1-6}$ alkyl or heteroalkyl;
$R_3$ and $R_4$ are, independently, H or $(CH_2)_nR$ where R is aryl and n=1-6;
$R_5$ is $(CH_2)_{n'''}N(R_3)_2$ or $(CH_2)_{n'''}COX$ wherein X is R''', OR''', SR''', NHR''' or $N(R''')_2$, wherein n'''=0-6, and R''' is independently H, or branched or unbranched $C_{1-6}$ alkyl or heteroalkyl; and
$R_6$ is quinoline or isoquinoline, partially or fully hydrated, and optionally substituted with $R^{IV}$, $OR^{IV}$, $SR^{IV}$, $(CH_2)_{n^{IV}}NHR^{IV}$ or $(CH_2)_{n^{IV}}N(R^{IV})_2$, wherein $n^{IV}$=0-6, and $R^{IV}$ is independently H, or branched or unbranched $C_{1-6}$ alkyl or heteroalkyl;
or a pharmaceutically acceptable salt thereof.

2. The compound of claim 1, wherein $R_1$ is isoquinoline, partially or fully hydrated, and optionally substituted with R', OR', SR', $(CH_2)_{n'}NHR'$ or $(CH_2)_{n'}N(R)_2$, wherein n'=0-6, and R' is independently H, or branched or unbranched $C_{1-6}$ alkyl or heteroalkyl.

3. The compound of claim 2, wherein in $R_1$, isoquinoline is fully hydrated.

4. The compound of claim 1, wherein in $R_1$, isoquinoline is substituted with $(CH_2)_{n'}NHR'$ or $CH_2NHR'$.

5. The compound of claim 1, wherein R' is branched or unbranched $C_{1-6}$ alkyl.

6. The compound of claim 1, wherein R' is branched $C_4$ alkyl.

7. The compound of claim 1, wherein $R_1$ has the structure

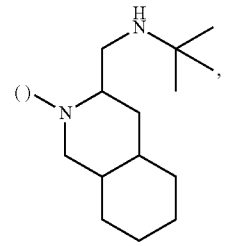

where ( ) represents the point of attachment to the molecular scaffold.

8. The compound of claim 1, wherein $R_2$ is R" or OR".

9. The compound of claim 1, wherein $R_2$ is OH.

10. The compound of claim 1, wherein $R_3$ is $(CH_2)_nR$.

11. The compound of claim 1, wherein $R_3$ is benzyl.

12. The compound of claim 1, wherein $R_4$ is H.

13. The compound of claim 1, wherein $R_5$ is $(CH_2)_{n'''}N(R_3)_2$.

14. The compound of claim 1, wherein $R_5$ is $(CH_2)_2NH_2$.

15. The compound of claim 1, wherein m=1.

16. The compound of claim 1, wherein $R_6$ is quinoline, partially or fully hydrated, and optionally substituted with $R^{IV}$, $OR^{IV}$, $SR^{IV}$, $(CH_2)_{n^{IV}}NHR^{IV}$ or $(CH_2)_{n^{IV}}N(R^{IV})_2$, wherein $n^{IV}$=0-6, and $R^{IV}$ is independently H, or branched or unbranched $C_{1-6}$ alkyl or heteroalkyl.

17. The compound of claim 1, wherein in $R_6$, quinoline is partially hydrated.

18. The compound of claim 1, wherein in $R_6$, the partially hydrated quinoline is 1,2,3,4-tetrahydroquinoline.

19. The compound of claim 1, wherein in $R_6$, quinoline is substituted with $R^{IV}$ or $OR^{IV}$.

20. The compound of claim 1, wherein in $R_6$, quinoline is substituted with OH.

21. The compound of claim 1, wherein $R_6$ has the structure

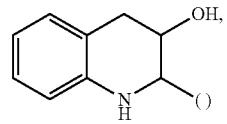

where ( ) represents the point of attachment to the molecular scaffold.

22. The compound of claim 1 having the structure

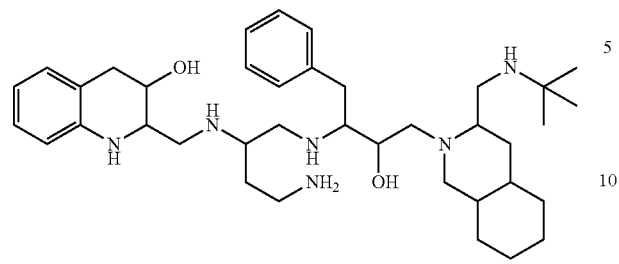

or a pharmaceutically acceptable salt thereof.

23. The compound of claim 1, wherein the compound is tagged with a radioisotope or a toxin.

24. The compound of claim 1, wherein the compound is coupled to an antibody or Fc backbone.

25. A pharmaceutical composition comprising the compound of claim 1 and a pharmaceutically acceptable carrier.

26. A method of treating systemic lupus erythematosus (SLE) in a subject comprising administering the compound of claim 1 to the subject in an amount and manner effective to treat SLE.

* * * * *